US009586874B2

(12) United States Patent
Zilbershtein et al.

(10) Patent No.: US 9,586,874 B2
(45) Date of Patent: Mar. 7, 2017

(54) METHOD FOR THE ISOLATION OF OLEFIN OLIGOMERIZATION PRODUCTS AND THE DECOMPOSITION OF OLIGOMERIZATION CATALYST RESIDUES

(75) Inventors: Timur Mikhailovich Zilbershtein, Kazan (RU); Maxim Vladimirovich Lipskikh, Tomsk (RU); Vladislav Alexandrovich Kardash, Kurlek (RU); Vladlena Vladimirovna Suvorova, Tymen (RU)

(73) Assignee: Public Joint Stock Company "Sibur Holding", Tobolsk (RU)

( * ) Notice: Subject to any disclaimer, the term of this patent is extended or adjusted under 35 U.S.C. 154(b) by 470 days.

(21) Appl. No.: 14/128,352

(22) PCT Filed: Jun. 21, 2012

(86) PCT No.: PCT/RU2012/000484
§ 371 (c)(1),
(2), (4) Date: Dec. 20, 2013

(87) PCT Pub. No.: WO2012/177183
PCT Pub. Date: Dec. 27, 2012

(65) Prior Publication Data
US 2014/0121435 A1 May 1, 2014

(30) Foreign Application Priority Data

Jun. 22, 2011 (RU) .................... 2011125946

(51) Int. Cl.
| | | |
|---|---|---|
| C07C 2/08 | (2006.01) | |
| C07C 2/22 | (2006.01) | |
| C07C 2/26 | (2006.01) | |
| C07C 2/30 | (2006.01) | |
| C07C 2/32 | (2006.01) | |
| C07C 7/17 | (2006.01) | |
| C07C 7/20 | (2006.01) | |
| C07C 7/04 | (2006.01) | |
| B01J 31/14 | (2006.01) | |
| B01J 31/18 | (2006.01) | |

(52) U.S. Cl.
CPC .................. *C07C 7/04* (2013.01); *C07C 2/32* (2013.01); *B01J 31/143* (2013.01); *B01J 31/181* (2013.01); *B01J 2231/20* (2013.01); *B01J 2531/62* (2013.01); *C07C 2531/14* (2013.01); *C07C 2531/22* (2013.01); *C07C 2531/34* (2013.01); *Y02P 20/52* (2015.11); *Y02P 20/584* (2015.11)

(58) Field of Classification Search
CPC .... C07C 2/08; C07C 2/22; C07C 2/24; C07C 2/26; C07C 2/30; C07C 2/32; C07C 7/17; C07C 7/20
USPC ....... 585/511, 512, 513, 521, 522, 523, 527, 585/809, 833, 842, 856, 860
See application file for complete search history.

(56) References Cited

U.S. PATENT DOCUMENTS

| 5,750,816 A | 5/1998 | Araki et al. |
|---|---|---|
| 2010/0113851 A1 | 5/2010 | Kreischer et al. |

FOREIGN PATENT DOCUMENTS

| RU | 2 123 501 | 12/1998 |
|---|---|---|
| RU | 2 131 405 | 6/1999 |
| RU | 2249585 | 1/2004 |
| WO | WO-99/19280 | 4/1999 |

OTHER PUBLICATIONS

International Search Report mailed Nov. 1, 2012, directed to International Application No. PCT/RU2012/000484; 2 pages.

*Primary Examiner* — Thuan D Dang
(74) *Attorney, Agent, or Firm* — Morrison & Foerster LLP

(57) ABSTRACT

The invention relates to the production of olefin oligomers by a method of oligomerization of olefins, and, in particular, to a method of isolating olefin oligomerization products and decomposing the oligomerization catalyst residues. The method of isolating products of an oligomerization reaction of olefins including a terminal double bond, in which the reaction is carried out by the action of a catalyst having chromium compounds, a nitrogen-containing ligand and organoaluminum compounds, includes a step of isolating independent olefin products and a step of treating catalyst residues. Further, the method includes the following sequential steps:
  a) isolating at least one liquid product of the oligomerization reaction of olefins from an output stream of an oligomerization reactor;
  b) treating a residue with an aqueous solution of an acid; and
  c) separating an organic layer and an aqueous layer.

17 Claims, No Drawings

METHOD FOR THE ISOLATION OF OLEFIN OLIGOMERIZATION PRODUCTS AND THE DECOMPOSITION OF OLIGOMERIZATION CATALYST RESIDUES

REFERENCE TO RELATED APPLICATIONS

This application is a national stage application under 35 USC 371 of International Application No. PCT/RU2012/000484, filed Jun. 21, 2012, which claims the priority of Russian Patent Application No. 2011125946, filed Jun. 22, 2011, the entire contents of which are incorporated herein by reference.

FIELD OF THE INVENTION

The invention relates to the field of producing olefin oligomers. They are a widely used as copolymers, a raw material for the preparation of oils and lubricants, a raw material for the preparation of other chemical products. More specifically, the invention relates to a production of olefin oligomers by an olefin trimerization process.

BACKGROUND OF THE INVENTION

An oligomerization reaction is usually carried out as a homogenous catalytic process in the presence of metallorganic catalysts. The output stream of an oligomerization reactor usually is a mixture of olefin oligomers, namely, reaction products, an initial olefin, a catalyst and/or residues thereof and often a solvent. In order to separate reaction products, various methods are used in this field of the art. For example, Russian patent No. 2131405 describes a method of isolating products of a trimerization reaction of olefins, said products being obtained by means of a catalyst comprising chromium compounds and organoaluminum compounds; the method comprising contacting a reaction product stream from the outlet of a reactor with an alcohol, in the course of which a catalyst system is deactivated. After that, the olefin product is separated, and a residue is contacted with an aqueous base, thereby forming a chromium-containing solid sediment. Then, the solid sediment, an aqueous layer and an organic layer are separated with subsequent addition of a mineral acid to an aqueous phase. A drawback of the method is the presence of an alcohol in the reaction mixture, which can result in the residues of this alcohol ending up in an olefin product and in a recurrent solvent if it is used, which, in turn, leads to impairing of the quality thereof. In addition, heavy olefin products can be contaminated with this alcohol during the treatment hereof with an acid. Furthermore, the use of the indicated method results in the complication of the scheme and the control system of the process because it is necessary to thoroughly control a proportion of alcohol and/or amine, to add firstly the alkaline solution before adding the acidic solution, and to separate the precipitated sediment.

Russian patent No. 2249585 mentions another drawback of the aforesaid method, namely, the isolation of hydrogen halide in the presence of alkyl-aluminum halides in the catalyst system. Therefore, the solution is further improved by adding an amine, instead of an alcohol or in addition to an alcohol, to bind a released hydrogen halide. However, this entails an additional complication of the scheme and the necessity to utilize/isolate residues of the amine or a salt thereof.

U.S. Pat. No. 5,750,816 describes the solution that is closest to the proposed one, said solution optionally includes addition of alcohol, amine, phenol, carboxylic acid and other compounds for the maintenance of the catalyst components in a dissolved state. At the same time, the use of these components is not obligatory. In order to simplify the scheme, a by-product polymer that is usually formed in a trimerization reaction is not separated from the reaction product stream before a distillation column, wherein the separation of the reaction products and a solvent when used from residues of the catalyst and the by-product polymer isolated in the solid state is carried out. At the same time, the content of the column bottom is heated to a temperature of 200° C. or more to separate high-boiling reaction products. It is noted that the preliminary separation of the polymer before the distillation step in this method results in the sedimentation of the catalyst residues in the form of a resin on the surface of a heater and in impairing the operation thereof. A drawback of this method is the formation of a solid residue after the distillation, said residue comprising by-product polymer and catalyst residues, and it is difficult to utilize said residue because a fine-dispersed polymer contaminated with the catalyst residues is capable of holding a significant amount of substances comprised in the catalyst residues, due to adsorption and/or absorption. This hampers their isolation by conventional methods such as the treatment with acidic or alkaline, aqueous or organic solution. Furthermore, the presence of a dispersed by-product polymer in the stream of products from the reactor to the distillation column requires the maintenance of an increased temperature or other methods making it possible to avoid the sedimentation of a polymer in the line and in apparatuses which are present in the production line, including measuring devices.

The problem to be solved within the scope of the present invention is an isolation of products of an oligomerization reaction of olefins comprising a terminal double bond, from the output stream of an oligomerization reactor, and a separation of a polymeric by-product and catalyst residues, including aluminum and chromium compounds.

In order to solve the problem, a method is provided that does not comprise adding any agents to deactivate a catalyst system, wherein the method consists in isolation of products of an oligomerization reaction of olefins comprising a terminal double bond, said reaction being conducted by the action of a catalyst comprising chromium compounds, a nitrogen-containing ligand and organoaluminum compounds, said method comprising the following three sequential steps:

a) isolating at least one liquid product of the oligomerization reaction of olefins from an output stream of an oligomerization reactor;

b) treating a residue with an aqueous solution of an acid; and c) separating an organic layer and an aqueous layer.

The problem is solved by a method that does not comprise adding any agents for deactivating a catalyst system. The method comprises the step of separating a by-product polymer from the output stream of an oligomerization reactor before feeding the stream into a distillation column. The distillation is carried out stepwise, at first isolating at least one olefin reaction product. In order to avoid the formation of a resin during the distillation of high-boiling reaction products after the step of separating at least one olefin, a mixture that is formed after the separation and comprises the high-boiling reaction products, is treated with an aqueous solution of an acid to separate catalyst residues, first of all aluminum and chromium compounds, in the form of water-soluble salts, with subsequent separation of aqueous and organic phases. Then, the organic phase may be fed to the next distillation step to isolate high-boiling products.

Firstly, the use of the proposed methods allows the isolation of target reaction products, avoiding the ingress of impurities of foreign substances, such as alcohols into products and/or recurrent solvent, and elimination of the necessity of the separation of these foreign substances. Secondly, the use of the proposed method makes it possible to avoid the contamination of lines and devices between the reactor and the distillation column with a side product. Thirdly, the solution makes it possible to separate catalyst residues from a polymer by-product, thus facilitating the regeneration of the catalyst or separation of metal compounds from catalyst residues, while avoiding the precipitation of a resin during the distillation of the high-boiling reaction products. Thus, the proposed solution makes it possible to achieve results exceeding or at least comparable with earlier known methods, and avoiding drawbacks inherent herein.

DETAILED DESCRIPTION OF THE INVENTION

It is most preferable to use the proposed invention for oligomerization of olefins comprising a terminal double bond, such as ethylene, propylene, butene-1, hexene-1.

Now the great quantity of methods using different catalysts and catalyst systems mainly comprising chromium compounds is proposed for carrying out the oligomerization reaction. According to the claimed method, it is preferable to use catalysts with a high activity and selectivity to target oligomerization products to improve the efficiency of the process.

All the steps of the manufacture of an oligomerization catalyst system are preferably conducted under conditions excluding the contact of the components of the catalyst system with water and atmospheric oxygen. Especially, it is recommended to avoid the contact of an organoaluminum compound and oligomerization catalyst system with moisture and oxygen after mixing all components of the oligomerization catalyst system, including an organoaluminum compound. The contamination of the catalyst with traces of moisture and/or oxygen may result in an increased formation of a by-product polymer, thus impeding the process of isolating oligomerization products of olefins.

It is preferable that the high active catalyst system for conducting the oligomerization reaction is prepared with the use of a chromium source, a nitrogen-containing ligand, an organoaluminum compound, a halogen-containing compound, and using SHF-radiation exposure. However, other known high-active oligomerization catalyst systems are contemplated in carrying out the invention.

Any organic or inorganic chromium compound or a mixture of these compounds may be used as a chromium source. An oxidation state of chromium in the indicated compounds may vary within a range of from 0 to 6. Generally, the chromium source has the formula $CrX_n$, wherein substituents X may be the same or different and may represent an organic or inorganic residue, and n is an integer from 1 to 6. The organic residues may comprise from 1 to 20 carbon atoms in one residue and are selected from the group consisting of an alkoxy group, alkylcarboxylic and ketonic residues, pyrrolide and an amide moiety. The inorganic residues comprise, but are not limited to, for example, halides, sulfates and/or oxides. Examples of the chromium compounds include, but are not limited to, for example, chromium (III) chloride, chromium (III) acetate, chromium (III) tris-ethylhexanoate, chromium (III) acetylacetonate, chromium (III) pyrrolide, and chromium (II) acetate.

In order to increase the selectivity of the catalyst system to hexene-1, halogen-containing compounds are preferably used as an additional component of the oligomerization catalyst system, the halogen-containing compounds having general formula $RmXn$, wherein R is an organic or inorganic radical, X is fluoro, chloro, bromo, or iodo, m+n>0. $AlEt_2Cl$, $AlEtCl_2$, and $CHCl_3$ may serve as examples of such compounds.

The nitrogen-containing ligand may be an organic compound including a pyrrole ring fragment, i.e. a five-membered aromatic ring having one nitrogen atom. Examples of the nitrogen-containing ligands include, but are not limited to, pyrrole, 2,5-dimethylpyrrol, lithium pyrrolide $C_4H_4NLi$, 2-ethylpyrrol, indole, 2-methylindole, and 4,5,6,7-tetrahydroindole. The use of pyrrole or 2,5-dimethylpyrrole is most preferable.

The organoaluminum compound may be an alkylaluminum compound, a halogenated alkylaluminum compound, an alkoxyalkylaluminum compound and mixtures thereof. The organoaluminum compound should include both at least one non-hydrolyzed compound represented by the general formulae $AlR_3$, $AlR_2X$, $AlRX_2$, $AlR_2OR$, $AlRXOR$ and/or $Al_2R_3X_3$, wherein R is an alkyl group, X is a halogen atom. Examples of these compounds include, but are not limited to, triethylaluminum, diethylaluminum chloride, tripropylaluminum, triisobutylaluminum, diethylaluminum ethoxide and/or ethylaluminum sesquichloride. Triethylaluminum or a mixture of triethylaluminum and diethylaluminum chloride is the most preferable organoaluminum compound.

In order to increase the activity of the catalyst system, it is preferable to use exposure of the organoaluminum compound and the halogen-containing compound by SHF-radiation. Preferably, the organoaluminum compound, and also optionally halogenide, optionally in the form of a solution in a hydrocarbon solvent, are exposed by SHF-radiation, and then are mixed with the chromium source and nitrogen-containing ligand. The addition of halogenide is optional, but provides the best results. In the course of the exposure, the exposed material or a mixture of substances should be in a vessel transparent for the SHF-radiation, for example, in a glass, fluoroplastic, or polypropylene vessel. The radiation power and time of the exposure may be arbitrary. However, for the best results, the time of the exposure of from 30 sec to 20 minutes, and the SHF-radiation nominal power of from 100 to 50000 W per 1 gram of the used organoaluminum compounds in terms of the elementary aluminum are preferable. Such exposure does not generally result in heating an organoaluminum compound or a solution thereof more than for 10° C. The time of the exposure of more than 20 minutes usually does not provide additional advantages for the properties of the obtained trimerization catalyst system. The time of the exposure of less than 30 sec may be insufficient to provide significant alterations in the properties of the organoaluminum compound and, optionally, halide, which, in turn, provides an insufficient increase in activity and/or selectivity of the catalyst system thereby obtained.

It is preferable to minimize the time between the termination of the exposure and the beginning of the mixing of an organoaluminum compound and, optionally, halide with a chromium source and a nitrogen-containing ligand. It is desirable that the indicated time is less than 1 minute. If this time is more than 3 minutes, the properties of the obtained catalyst system may worsen as compared with the system prepared of the SHF-radiated organoaluminum compound which was added less than one minute after the termination of the exposure. In particular, the activity of the obtained catalyst system may decrease. If a period of time between the termination of the exposure and the beginning of the mixing is more than 20 minutes, there is no a significant difference between the catalyst systems obtained with using an SHF-radiated organoaluminum compound and the catalyst systems obtained with using an aluminum-containing compound that was not exposed by the SHF-radiation.

In general, to obtain the oligomerization catalyst system, 1 mole of chromium based on elemental chromium may be admixed with 1-50 moles of a nitrogen-containing ligand and 1-250 moles of an organoaluminum compound based on elemental aluminum in the excess of an unsaturated hydrocarbon. If a halide source is used, its amount is usually from 1 to 60 moles based on the element (halogen). It is preferable to use 1 mole of chromium based on elemental chromium admixed with 2-8 moles of a nitrogen-containing ligand and 10-80 moles of aluminum based on elemental aluminum in the excess of the unsaturated hydrocarbon. If a halogen source is present, its amount of from 1 to 20 moles of halide based on elemental halogen is preferable.

The oligomerization reaction may be carried out by any method known in the art, using an oligomerization catalyst system. The above described catalyst system is preferable due to high activity and selectivity thereof.

It is preferable to use an aliphatic hydrocarbon solvent that does not comprise a significant amount of unsaturated compounds since it may worsen conducting the oligomerization reaction and complicate the isolation of the reaction products because of an increased formation of a by-product polymer. It is the most preferable to use a hydrocarbon solvent that is saturated compound and is not an oligomerization product or initial olefin. Heptane, cyclohexane, pentane, cyclopentane, butane, decane, methylcyclohexane may serve as examples of such a solvent. It is also possible to use other hydrocarbon solvents.

It is preferable that hydrogen be present in the reaction mixture when carrying out the oligomerization reaction. This reduces both the total amount of a by-product polymer formed and an amount of polymer precipitated on the reactor walls. This, in turn, facilitates the separation of stream coming out of the oligomerization reactor from the by-product polymer.

It is preferable to separate the output stream of the oligomerization reactor from a solid phase before the isolation of a liquid oligomerization product.

The output stream of the oligomerization reactor may be separated from a by-product polymer before the step of separating gaseous olefins (degassing step), if present, or after the degassing step. The by-product polymer may be separated by any known separation method, for example, by centrifugation or filtration.

After filtration and degassing, when used, the stream from the oligomerization reaction is directed to the step of separating products, in the course of which at least one olefin product is isolated. For example, if ethylene is used as an initial olefin, then usually a main oligomerization product, namely hexene, is separated at the step of distilling. To improve the process efficiency, it is also advisable to recycle the used solvent. The separation may be carried out by any method, but distillation is believed to be most simple and convenient. Different apparatuses for distillation may be used making it possible to isolate the reaction products and a solvent on one or more columns. At the same time, semi-volatile products having a molecular weight more than 4 times the molecular weight of an initial olefin should not be separated at this step from the catalyst residues.

Then, the bottom residue after the distillation of the olefin product, and optionally a solvent, is treated with an aqueous solution of an acid. It is recommended to use, as the acid, acids having the acid value pKa of not more than 7, for example, acetic acid, formic acid, phosphoric acid or other acids. It is recommended to use acids, aluminum and chrome salts of which have a solubility of not less than 10 g/l in water. Due to this, the aluminum and chromium compounds pass to an aqueous solution and may be used for the regeneration or safe utilization. The organic phase free of aluminum and chromium compounds is separated from the aqueous phase by conventional methods and then said phase is optionally separated by distillation to isolate a residual amount of volatile reaction products, a solvent and heavy reaction products.

In order to reduce the amount of wastes formed, it is preferable to remove chromium and aluminum ions from an aqueous solution and to increase the concentration of acid in the solution, thus allowing the re-use of the aqueous solution for treating the bottom residue. In order to purify the aqueous solution from chromium and aluminum ions, it is possible to use, for example, a cation-exchange resin making it possible to precipitate chromium and aluminum ions and regenerate the acid. Many acids are known to form complex ions with chromium ions, and these complex ions are deposited on the cation-exchange column in an insufficient degree. Therefore, in case of the use of a cation-exchange column to isolate chromium and aluminum ions, sulfuric, hydrochloric, nitric, chloric and other acids are preferable since anions of these acids do not form complex ions with the chromium cations.

When an aqueous solution used for the treatment of the distillation residue passes through a cation-exchange column (for example, KU-2-8 according to State Standard 20298-74), aluminum and chromium salts are precipitated on the cation-exchange column, and the concentration of acid in the aqueous solution increases up to a value close to the acid concentration in the initial aqueous solution before the treatment of the bottom residue. This makes it possible to re-use the aqueous solution after passing the ion-exchange column for treating the bottom residue. Chromium and aluminum ions may be isolated by known procedures of regeneration of cation-exchange columns, for example, by washing with a 10-20% aqueous solvent of sulfuric acid.

To provide a better understanding of the proposed technical solution, examples of embodiments of the invention are presented below. They are provided only to illustrate the invention, and are not intended to limit the scope of the invention.

Example 1

55.5 mg (0.115 mM) of chromium (III) ethylhexanoate ($Cr(EH)_3$) and 54.9 mg (0.575 mM) of 2,5-dimethylpyrrole (DMP) are admixed in 10 ml of ethylbenzene in a dry flask filled with nitrogen. A solution of tri-ethyl aluminum (TEA) in toluene (1.9 mole/l) in an amount of 2.25 ml (4.28 mM) is admixed with a solution of diethylaluminum chloride (DEAC) in hexane (1.0 mole/l) in an amount of 1.5 ml (1.5 mM). The obtained mixture of organoaluminum compounds is exposed by SHF-radiation for 6 minutes at a nominal power of 400 W. Then, the solution of TEA and DEAC is added to a mixture of ethylbenzene, DMP and $Cr(EH)_3$ for 30 seconds to obtain a brown solution which after 15 minutes gains the orange-yellow colour. The solvents are removed under vacuum. The residue is diluted with 10 ml of cyclohexane and then is additionally diluted with cyclohexane up to the volume of 2.00 l. The obtained solution of the catalyst system having chromium concentration of 3.0 mg/l is used in the trimerization reaction of ethylene.

140 ml of a solvent of the catalyst system is added to a 0.5 l reactor, hydrogen is added to achieve a partial pressure of 0.5 bar, and then ethylene is fed, wherein the total pressure of 15 bars (gauge) is maintained in the system for 35 minutes. Ethylene absorption is 29.1 g. Then, the catalyst system solution and hydrogen are fed at rates of 140 g/h and 0.2 nl/h, respectively, and the reactor is discharged at a rate equal to the sum of the rates of feeding ethylene and the catalyst system solution. The output stream of the reactor is passed through a filter and a flow regulator and is directed to a degasser. The liquid phase from the degasser is fed to rectification, and a main reaction product (hexene-1), a solvent (cyclohexane) and heavy reaction products together with the catalyst residues are isolated. After the beginning of the discharge of the reactor, the reaction is carried out for 5 hours.

Heavy reaction products comprising catalyst residues are separated from the bottom residue and are mixed with a 10%-aqueous solution of acetic acid in an amount of 25 ml per 100 ml of the bottom residue, providing an effective contact between phases. The aqueous solution and the precipitate are separated from the organic solution. 50 ml of a 10% solution of $Na\ CO_3$ are added to the aqueous solution and the precipitate. The brown precipitate is filtrated and dried on air. The results of the reaction are presented in Table 1.

Example 2

74.0 mg (0.154 mM) of $Cr(EH)_3$ and 73.2 mg (0.769 mM) of DMP are admixed in 10 ml of ethylbenzene in a dry flask filled with nitrogen. A solution of TEA in toluene (1.9 mole/l) in an amount of 2.9 ml (5.51 mM) is admixed with a DEAC solution in hexanes (1.0 mole/l) in an amount of 2.15 ml (2.15 mM). The obtained mixture of organoaluminum compounds is exposed by SHF-radiation for 6 minutes at a nominal power of 400 W. Then, the solution of TEA and DEAC is added to a mixture of ethylbenzene, DMP and $Cr(EH)_3$ for 30 seconds, to obtain a brown solution which after 15 minutes gains orange-yellow colour. The solvents are removed under vacuum. The residue is diluted with 10 ml of cyclohexane and then is additionally diluted with cyclohexane up to the volume of 2.00 l. The obtained solution of the catalyst system having the chromium concentration of 4.0 mg/l is used in the trimerization reaction of ethylene.

170 ml of a solvent of the catalyst system is added to a 0.5 l reactor, hydrogen is added to achieve a partial pressure of 0.5 bar, and then ethylene is fed, wherein the total pressure equal to 9 bars is maintained in the system for 30 minutes. The absorption of ethylene is 21.1 g. Then, the catalyst system solution and hydrogen are fed at a rate of 165 g/h and 0.2 nl/h, respectively, and the reactor is discharge at a rate equal to the sum rate of the rates of feeding ethylene and the catalyst system solution. The output stream of the reactor is passed through a filter and a flow regulator and is directed to a degasser. The liquid phase from the degasser is fed to rectification and a main reaction product (hexene-1), a solvent (cyclohexane) and heavy reaction products together with the catalyst residues are isolated. After the beginning of the discharge of the reactor, the reaction is carried out for 4 hours.

The heavy reaction products are reprocessed in the same way as in example 1. The results of the reaction are presented in table 1.

Example 3

74.0 mg (0.154 mM) of $Cr(EH)_3$ and 73.2 mg (0.769 mM) of DMP are admixed in 10 ml of ethylbenzene in a dry flask filled with nitrogen. A solution of TEA in toluene (1.9 mole/l) in an amount of 2.9 ml (5.51 mM) is admixed with a DEAC solution in hexanes (1.0 mole/l) in an amount of 2.15 ml (2.15 mM). Then, the solution of TEA and DEAC is added to a mixture of ethylbenzene, DMP and $Cr(EH)_3$ to obtain a brown solution, which after 15 minutes gains orange-yellow colour. The solvents are removed under vacuum. The residue is diluted with 10 ml of cyclohexane and then is additionally diluted with cyclohexane up to a volume of 2.00 l. The obtained solution of the catalyst system with the chromium concentration of 4.0 mg/l is used in the trimerization reaction of ethylene. 170 ml of solvent of the catalyst system is added to a 0.5 l reactor, hydrogen is added to achieve a partial pressure of 0.5 bar, and then ethylene is fed, wherein the total pressure of 12 bars (gauge) is maintained in the system for 30 minutes. The ethylene absorption is 36.5 g. Then, the catalyst system solution and hydrogen are fed at a rate of 165 g/h and 0.2 nl/h, respectively, and the reactor is discharge at a rate equal to the sum rate of the rates feeding of ethylene and the catalyst system solution. The output stream of the reactor is passed through a filter and a flow regulator and is directed to a degasser. The liquid phase from the degasser is fed to rectification and a main reaction product (hexene-1), a solvent (cyclohexane) and heavy reaction products together with the catalyst residues are isolated. After the beginning of the discharge of the reactor, the reaction is carried out for 4 hours.

The heavy reaction products are reprocessed in the same way as in example 1. The results of the reaction are presented in table 1.

Example 4

92.5 mg (0.192 mM) of $Cr(EH)_3$ and 91.5 mg (0.962 raM) of DMP are admixed in 15 ml of ethylbenzene in a dry flask filled with nitrogen. A solution of TEA in toluene (1.9 mole/l) in an amount of 3.75 ml (7.13 mM) is admixed with a DEAC solution in hexanes (1.0 mole/l) in an amount of 2.5 ml (2.50 mM). The obtained mixture of organoaluminum compounds is exposed by SHF-radiation for 6 minutes at a nominal power of 400 W. Then, the solution of TEA and DEAC is added to a mixture of ethylbenzene, DMP and $Cr(EH)_3$ for 30 seconds, to obtain a brown solution, which after 15 minutes gains orange-yellow colour. The solvents are removed under vacuum. The residue is diluted with 10 ml of cyclohexane and then is additionally diluted with cyclohexane up to the volume of 2.00 l. The obtained solution of the catalyst system having the chromium concentration of 4.0 mg/l is used in the trimerization reaction of ethylene.

150 ml of solvent of the catalyst system is added to a 0.5 l reactor, hydrogen is added to achieve a partial pressure of 0.5 bar, and then ethylene is fed, wherein the total pressure of bars (gauge) is maintained in the system for 30 minutes. Ethylene absorption is 27.7 g. Then, the catalyst system solution and hydrogen are fed at a rate of 165 g/h and 0.2 nl/h, respectively, and the reactor is discharged at a rate equal to the sum rate of the rates feeding of ethylene and the catalyst system solution. The output stream of the reactor is passed through a filter and a flow regulator and is directed to a degasser. The liquid phase from the degasser is fed to rectification and a main reaction product (hexene-1), a solvent (cyclohexane) and heavy reaction products together with the catalyst residues are isolated.

After the beginning of the discharge of the reactor, the reaction is carried out for 3 hours.

The heavy reaction products are reprocessed in the same way as in example 1. The results of the reaction are presented in table 1.

Example 5

Heavy reaction products comprising catalyst residues are taken out from the bottom residue and are admixed with a 3% aqueous solution of nitric acid in an amount of 60 ml per 100 ml of the bottom residue, thereby providing an effective contact of phases. A possible precipitate is filtrated. The aqueous and organic solvents are separated. The aqueous solution is passed through a column having a diameter of 2 cm, filled with a layer of cathionite KU-2-8 in H-form having a height of 30 cm, thus obtaining an aqueous solution purified from chromium and aluminum salts. The content of chromium and aluminum in the initial bottom residue, in the organic layer after the treatment with a nitric acid solution and separation of the aqueous solution, in the aqueous solution before the passing through the column with cathionite, and in the aqueous solution after passing thereof through the column with cathionite are analyzed by an inductively coupled plasma mass-spectrometry (ICP-MS) method. The content of aluminum and chromium in the solutions, in ppm, are presented in table 2.

TABLE 1

| Parameter | Example 1 | Example 2 | Example 3 | Example 4 |
|---|---|---|---|---|
| Concentration of Cr in the catalyst solution, mg/l | 3.0 | 4.0 | 4.0 | 5.0 |
| Cr:DMP:TEA:DEAC | 1:5:37:13 | 1:5:36:14 | 1:5:36:14 | 1:5:37:13 |
| Pressure of ethylene, bar | 15 | 9 | 12 | 9 |
| SHF-exposure, min. | 6 | 6 | 0 | 6 |
| Hexene-1, % | 89.2 | 87.9 | 87.1 | 84.4 |
| Other hexenes, % | 0.3 | 0.2 | 0.4 | 0.5 |
| Butenes, % | 0.7 | 1.3 | 1.2 | 0.7 |
| Octenes, % | 0.4 | 0.4 | 0.3 | 0.5 |
| Decenes, % | 8.6 | 9.2 | 9.8 | 12.0 |
| C12+, % | 0.8 | 0.8 | 1.2 | 1.9 |
| Hexene-1 purity in C6, % | 99.68 | 99.73 | 99.58 | 99.43 |
| Ethylene consumption, g/h | 64.2 | 56.0 | 79.2 | 83.4 |
| Chromium consumption, mg/h | 0.54 | 0.64 | 0.83 | 1.06 |
| Conversion of ethylene, % | 85 | 91 | 80 | 88 |
| The efficacy of catalyst, kg of olefins/g Cr | 100.1 | 79.6 | 75.9 | 69.2 |
| Residence time of the catalyst, h | 0.79 | 1.00 | 0.78 | 0.70 |
| The activity of catalyst, kg/(g Cr*h) | 126.7 | 79.6 | 97.3 | 98.9 |

TABLE 2

The content of aluminum and chromium in solutions, ppm

| Solution | Al | Cr |
|---|---|---|
| Initial bottom residue | 440 | 18 |
| Organic after the treatment with the diluted aqueous nitric acid | <1 | <1 |
| Aqueous after the treatment of the organic layer | 745 | 30 |
| Aqueous after the cathion-exchanger | <1 | <1 |

The invention claimed is:

1. A method for isolating products of an oligomerization reaction of olefins comprising a terminal double bond, wherein the reaction is carried out in an aliphatic hydrocarbon solvent, by the action of a catalyst comprising chromium compounds, a nitrogen-containing ligand and organoaluminum compounds, said method comprising a step of isolating individual olefin products and a step of treating catalyst residues, characterized in that the method comprises the following sequential steps:
   a) isolating at least one liquid product of the oligomerization reaction of olefins from an output stream of an oligomerization reactor;
   b) treating a residue formed in the isolating step of a) with an aqueous solution of an acid, the residue comprising a bottom residue after isolation of the liquid product and optionally the solvent; and
   c) separating an organic layer, and an aqueous layer that are formed in the treating step of b), the organic layer comprising heavy reaction products and optionally the solvent, and the aqueous layer comprising catalyst residues.

2. The method according to claim 1, characterized in that any acids having aluminum and chromium salts with the water solubility of not less than 10 g/l are used as the acid.

3. The method according to claim 1, characterized in that the catalyst prepared with using SHF-radiation exposure of organoaluminum compounds is used.

4. The method according to claim 1, characterized in that the olefin comprising a terminal double bond is ethylene, propylene, butene-1 or hexene-1.

5. The method according to claim 1, characterized in that the olefin comprising a terminal double bond is ethylene.

6. The method according to claim 1, characterized in that the hydrocarbon solvent is used that is a saturated compound and is not the oligomerization product or the initial olefin.

7. The method according to claim 1, characterized in that the organoaluminum compounds are an alkylaluminum compound.

8. The method according to claim 1, characterized in that the output stream of the oligomerization reactor is separated from a solid phase before the isolation of the liquid oligomerization product.

9. The method according to any of claims 1 to 8, characterized in that isolating the liquid product of oligomerization and isolating the solvent are carried out before the treatment with the aqueous solution of the acid.

10. A method of isolating products of an oligomerization reaction of olefins comprising a terminal double bond, wherein the reaction is carried out in an aliphatic hydrocarbon solvent, by the action of a catalyst comprising chromium-compounds, a nitrogen-containing ligand and organoaluminum compounds, said method comprising a step of isolating individual olefin products and a step of treating catalyst residues, characterized in that the method comprises the following sequential steps:

d) isolating at least one liquid product of the olefin oligomerization reaction from an output stream of an oligomerization reactor;

e) treating a residue formed in the isolating step of d) with an aqueous solution of an acid that does not form complex ions with chromium, the residue comprising a bottom residue after isolation of the liquid product and optionally the solvent;

f) separating an organic layer, and an aqueous layer that are formed in the treating step of e), the organic layer comprising heavy reaction products and optionally the solvent, and the aqueous layer comprising catalyst residues;

h) passing the aqueous layer through a cathion-exchange resin for regenerating the acid and separating aluminum and chromium ions.

11. The method according to claim 10, characterized in that a catalyst prepared with using SHF-radiation exposure of organoaluminum compounds is used.

12. The method according to claim 10, characterized in that the olefin comprising a terminal double bond is ethylene, propylene, butene-1 or hexene-1.

13. The method according to claim 10, characterized in that the olefin comprising a terminal double bond is ethylene.

14. The method according to claim 10, characterized in that the hydrocarbon solvent is used that is a saturated compound and is not the oligomerization product or the initial olefin.

15. The method according to claim 10, characterized in that the organoaluminum compounds are an alkylaluminum compound.

16. The method according to claim 10, characterized in that the output stream of the oligomerization reactor is separated from a solid phase before the isolation of the liquid product of oligomerization.

17. The method according to any of claims 10 to 16, characterized in that isolating the liquid product of oligomerization and isolating the solvent are carried out before the treatment with an aqueous solution of acid.

* * * * *